US008877829B2

(12) United States Patent
Schorzman et al.

(10) Patent No.: US 8,877,829 B2
(45) Date of Patent: Nov. 4, 2014

(54) PROCESS FOR MAKING CATIONIC HYDROPHILIC SILOXANYL MONOMERS

(75) Inventors: Derek A. Schorzman, Cary, NC (US); Joseph C. Salamone, San Antonio, TX (US); Daniel M. Ammon, Jr., Webster, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 1077 days.

(21) Appl. No.: 12/890,019

(22) Filed: Sep. 24, 2010

(65) Prior Publication Data

US 2011/0015298 A1    Jan. 20, 2011

Related U.S. Application Data

(62) Division of application No. 11/611,512, filed on Dec. 15, 2006, now Pat. No. 7,825,273.

(60) Provisional application No. 60/756,665, filed on Jan. 6, 2006.

(51) Int. Cl.
C08G 77/388    (2006.01)
C07F 7/08    (2006.01)

(52) U.S. Cl.
CPC ............ *C07F 7/0854* (2013.01); *C08G 77/388* (2013.01)
USPC ........................................ 523/107; 523/106

(58) Field of Classification Search
USPC ................................................. 523/107, 106
See application file for complete search history.

(56) References Cited

U.S. PATENT DOCUMENTS

| | | | |
|---|---|---|---|
| 3,808,179 A | 4/1974 | Gaylord | |
| 4,153,641 A | 5/1979 | Deichert et al. | |
| 4,686,267 A | 8/1987 | Ellis et al. | |
| 4,910,277 A | 3/1990 | Bambury et al. | |
| 5,034,461 A | 7/1991 | Lai et al. | |
| 5,070,215 A | 12/1991 | Bambury et al. | |
| 5,321,108 A | 6/1994 | Kunzler et al. | |
| 5,358,995 A | 10/1994 | Lai et al. | |
| 5,374,662 A | 12/1994 | Lai et al. | |
| 5,387,662 A | 2/1995 | Kunzler et al. | |
| 5,420,324 A | 5/1995 | Lai et al. | |
| 5,451,651 A | 9/1995 | Lai | |
| 5,496,871 A | 3/1996 | Lai et al. | |
| 5,539,016 A | 7/1996 | Kunzler et al. | |
| 5,594,085 A | 1/1997 | Lai | |
| 5,610,252 A | 3/1997 | Bambury et al. | |
| 5,639,908 A | 6/1997 | Lai | |
| 5,648,515 A | 7/1997 | Lai | |
| 7,468,397 B2 | 12/2008 | Schorzman | |
| 7,528,208 B2 | 5/2009 | Schorzman et al. | |
| 7,557,231 B2 | 7/2009 | Schorzman et al. | |
| 7,601,766 B2 | 10/2009 | Schorzman et al. | |
| 7,622,512 B2 | 11/2009 | Schorzman et al. | |

OTHER PUBLICATIONS

U.S. Appl. No. 11/341,209, filed Jan. 27, 2006, Schorzman et al.
U.S. Appl. No. 11/403,393, filed Apr. 13, 2006, Schorzman et al.
U.S. Appl. No. 11/480,111, filed Jun. 30, 2006, Schorzman et al.
U.S. Appl. No. 11/480,170, filed Jun. 30, 2006, Schorzman et al.
U.S. Appl. No. 11/611,508, filed Dec. 15, 2006, Schorzman et al.
U.S. Appl. No. 11/619,211, filed Jan. 3, 2007, Schorzman et al.
U.S. Appl. No. 11/830,885, filed Jul. 31, 2007, Schorzman et al.
U.S. Appl. No. 11/837,049, filed Aug. 10, 2007, Kunzier et al.
U.S. Appl. No. 11/840,650, filed Aug. 17, 2007, Salamone et al.
U.S. Appl. No. 12/018,910, filed Jun. 24, 2008, Stanbro et al.
U.S. Appl. No. 12/313,253, filed Nov. 18, 2008, Schorzman.
U.S. Appl. No. 12/459,778, filed Jul. 8, 2009, Kunzler et al.
U.S. Appl. No. 12/459,779, filed Jul. 8, 2009, Kunzler et al.
International Search Report (PCTISA/210) and Written Opinion (PCT/ISA/237) mailed on May 10, 2007.
William J. Benjamin, et al., The Oxygen Permeability of Reference Materials, Optom Vis Sci 7 (12s): 95 (1997).

*Primary Examiner* — Elvis O Price
(74) *Attorney, Agent, or Firm* — Toan P. Vo

(57) ABSTRACT

The present invention relates to polymeric compositions useful in the manufacture of biocompatible medical devices. More particularly, the present invention relates to certain cationic monomers capable of polymerization to form polymeric compositions having desirable physical characteristics useful in the manufacture of ophthalmic devices. Such properties include the ability to extract the polymerized medical devices with water. This avoids the use of organic solvents as is typical in the art. The polymeric compositions comprise polymerized cationic hydrophilic siloxanyl monomers prepared by the process disclosed herein.

16 Claims, 1 Drawing Sheet

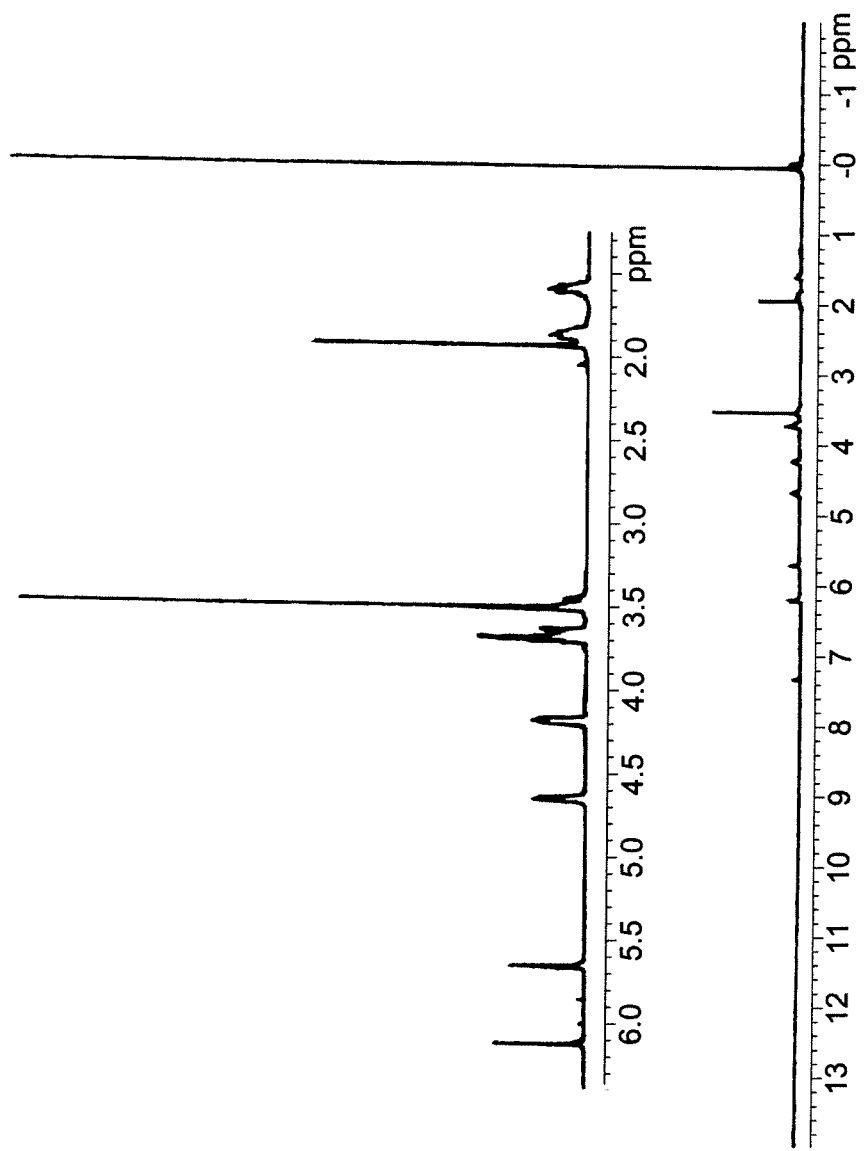

PROCESS FOR MAKING CATIONIC HYDROPHILIC SILOXANYL MONOMERS

PRIORITY CLAIMS TO PRIOR APPLICATIONS

This application is a divisional of U.S. Ser. No. 11/611,512 filed on Dec. 15, 2006, now U.S. Pat. No. 7,825,273, which claims the benefit of Provisional Patent Application No. 60/756,665 filed Jan. 6, 2006 the contents of which are incorporated herein by reference.

FIELD

The present invention relates to polymeric compositions useful in the manufacture of biocompatible medical devices. More particularly, the present invention relates to certain cationic monomers capable of polymerization to form polymeric compositions having desirable physical characteristics useful in the manufacture of ophthalmic devices. Such properties include the ability to extract the polymerized medical devices with water. This avoids the use of organic solvents as is typical in the art. The polymeric compositions comprise polymerized cationic hydrophilic siloxanyl monomers prepared by the process disclosed herein.

BACKGROUND AND SUMMARY

Various articles, including biomedical devices, are formed of organosilicon-containing materials. One class of organosilicon materials useful for biomedical devices, such as soft contact lenses, is silicon-containing hydrogel materials. A hydrogel is a hydrated, cross-linked polymeric system that contains water in an equilibrium state. Hydrogel contact lenses offer relatively high oxygen permeability as well as desirable biocompatibility and comfort. The inclusion of a silicon-containing material in the hydrogel formulation generally provides higher oxygen permeability; since silicon based materials have higher oxygen permeability than water.

Another class of organosilicon materials is rigid, gas permeable materials used for hard contact lenses. Such materials are generally formed of silicon or fluorosilicon copolymers. These materials are oxygen permeable, and more rigid than the materials used for soft contact lenses. Organosilicon-containing materials useful for biomedical devices, including contact lenses, are disclosed in the following U.S. Pat. No. 4,686,267 (Ellis et al.); U.S. Pat. No. 5,034,461 (Lai et al.); and U.S. Pat. No. 5,070,215 (Bambury et al.).

In addition, traditional siloxane-type monomers are hydrophobic and lenses made with them frequently require additional treatment to provide a hydrophilic surface. Although not wishing to be bound by a particular theory, the inventors believe that providing a charged siloxane-type monomer such as the quaternary siloxane-type monomers disclosed herein results in a hydrophilic siloxane-type monomer. It is believed that the hydrophilic quaternary groups interact with the electronegative portion of the polar water molecule.

Soft contact lens materials are made by polymerizing and crosslinking hydrophilic monomers such as 2-hydroxyethyl-methyacrylate, N-vinyl-2-pyrrolidone, and combinations thereof. The polymers produced by polymerizing these hydrophilic monomers exhibit significant hydrophilic character themselves and are capable of absorbing a significant amount of water in their polymeric matrices. Due to their ability to absorb water, these polymers are often referred to as "hydrogels". These hydrogels are optically clear and, due to their high levels of water of hydration, are particularly useful materials for making soft contact lenses. Siloxane-type monomers are well known to be poorly soluble in water as well as hydrophilic solvents and monomers and are therefore difficult to copolymerize and process using standard hydrogel techniques. Therefore, there is a need for new siloxane-type monomers that have improved solubility in the materials, specifically the diluents, used to make hydrogel lenses. Further there is a need for monomers that result in a polymerized medical device that is extractable in water instead of the organic solvents used in the prior art.

The present invention provides novel cationic organosilicon-containing monomers which are useful in articles such as biomedical devices including contact lenses.

BRIEF DESCRIPTION OF THE DRAWINGS

FIG. 1 is the NMR Spectra of a monomer prepared according to Example 1.

DETAILED DESCRIPTION

In a first aspect, the invention relates to monomers having the following analytical characteristics:

The monomers will also have as a counter ion $X^-$ which is at least a single charged counter ion. Examples of single charge counter ions include the group consisting of $Cl^-$, $Br^-$, $I^-$, $CF_3CO_2^-$, $CH_3CO_2^-$, $HCO_3^-$, $CH_3SO_4^-$, p-toluenesulfonate, $HSO_4^-$, $H_2PO_4^-$, $NO_3^-$, and $CH_3CH(OH)CO_2^-$. Examples of dual charged counter ions would include $SO_4^{2-}$, $CO_3^{2-}$ and $HPO_4^{2-}$. Other charged counter ions would be obvious to one of ordinary skill in the art. It should be understood that a residual amount of counter ion may be present in the hydrated product. Therefore, the use of toxic counter ions is to be discouraged. Likewise, it should be understood that, for a singularly charged counter ion, the ratio of counter ion and quaternary siloxanyl will be 1:1. Counter ions of greater negative charge will result in differing ratios based upon the total charge of the counter ion.

A schematic representation of a synthetic method for making the novel cationic silicon-containing monomers disclosed herein is provided below:

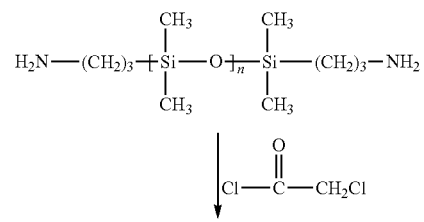

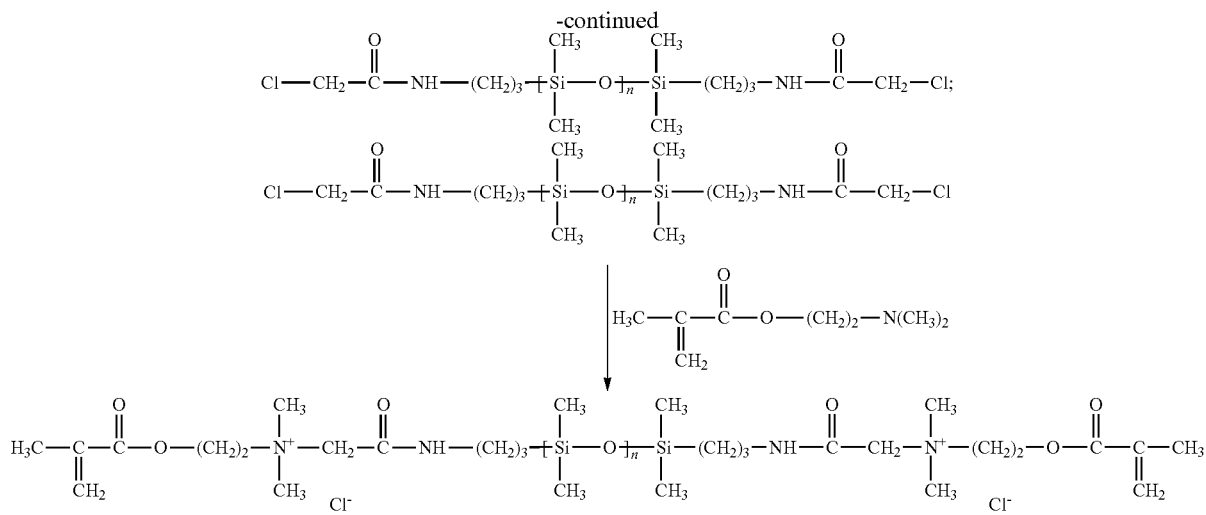

In a second aspect, the invention includes articles formed of device forming monomer mixes comprising the monomers made by the process described above. According to preferred embodiments, the article is the polymerization product of a mixture comprising the aforementioned monomers and at least a second monomer. Preferred articles are optically clear and useful as a contact lens.

Useful articles made with these materials may require hydrophobic, possibly silicon containing monomers. Preferred compositions have both hydrophilic and hydrophobic monomers. The invention is applicable to a wide variety of polymeric materials, either rigid or soft. Especially preferred polymeric materials are lenses including contact lenses, phakic and aphakic intraocular lenses and corneal implants although all polymeric materials including biomaterials are contemplated as being within the scope of this invention. Especially preferred are silicon containing hydrogels.

The present invention also provides medical devices such as heart valves, films, surgical devices, vessel substitutes, intrauterine devices, membranes, diaphragms, surgical implants, blood vessels, artificial ureters, artificial breast tissue and membranes intended to come into contact with body fluid outside of the body, e.g., membranes for kidney dialysis and heart/lung machines and the like, catheters, mouth guards, and denture liners, ophthalmic devices.

Silicon-containing hydrogels are prepared by polymerizing a mixture containing at least one silicon-containing monomer and at least one hydrophilic monomer. The silicon-containing monomer may function as a crosslinking agent (a crosslinker being defined as a monomer having multiple polymerizable functionalities) or a separate crosslinker may be employed.

An early example of a silicon-containing contact lens material is disclosed in U.S. Pat. No. 4,153,641 (Deichert et al assigned to Bausch & Lomb Incorporated). Lenses are made from poly(organosiloxane) monomers which are α, ω terminally bonded through a divalent hydrocarbon group to a polymerized activated unsaturated group. Various hydrophobic silicon-containing prepolymers such as 1,3-bis(methacryloxyalkyl)-polysiloxanes were copolymerized with known hydrophilic monomers such as 2-hydroxyethyl methacrylate (HEMA).

U.S. Pat. No. 5,358,995 (Lai et al) describes a silicon-containing hydrogel which is comprised of an acrylic ester-capped polysiloxane prepolymer, polymerized with a bulky polysiloxanylalkyl (meth)acrylate monomer, and at least one hydrophilic monomer. Lai et al is assigned to Bausch & Lomb Incorporated and the entire disclosure is incorporated herein by reference. The acrylic ester-capped polysiloxane prepolymer, commonly known as $M_2 D_x$ consists of two acrylic ester end groups and "x" number of repeating dimethylsiloxane units. The preferred bulky polysiloxanylalkyl (meth)acrylate monomers are TRIS-type (methacryloxypropyl tris(trimethylsiloxy)silane) with the hydrophilic monomers being either acrylic- or vinyl-containing.

Other examples of silicon-containing monomer mixtures which may be used with this invention include the following: vinyl carbonate and vinyl carbamate monomer mixtures as disclosed in U.S. Pat. Nos. 5,070,215 and 5,610,252 (Bambury et al); fluorosilicon monomer mixtures as disclosed in U.S. Pat. Nos. 5,321,108; 5,387,662 and 5,539,016 (Kunzler et al); fumarate monomer mixtures as disclosed in U.S. Pat. Nos. 5,374,662; 5,420,324 and 5,496,871 (Lai et al) and urethane monomer mixtures as disclosed in U.S. Pat. Nos. 5,451,651; 5,648,515; 5,639,908 and 5,594,085 (Lai et al), all of which are commonly assigned to assignee herein Bausch & Lomb Incorporated, and the entire disclosures of which are incorporated herein by reference.

Examples of non-silicon hydrophobic materials include alkyl acrylates and methacrylates.

The cationic silicon-containing monomers may be copolymerized with a wide variety of hydrophilic monomers to produce silicon hydrogel lenses. Suitable hydrophilic monomers include: unsaturated carboxylic acids, such as methacrylic and acrylic acids; acrylic substituted alcohols, such as 2-hydroxyethylmethacrylate and 2-hydroxyethylacrylate; vinyl lactams, such as N-vinyl pyrrolidone (NVP) and 1-vinylazonan-2-one; and acrylamides, such as methacrylamide and N,N-dimethylacrylamide (DMA).

Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art.

Hydrophobic cross-linkers would include methacrylates such as ethylene glycol dimethacrylate (EGDMA) and allyl methacrylate (AMA). In contrast to traditional silicon hydrogel monomer mixtures, the monomer mixtures containing the quaternized silicon monomer of the invention herein are relatively water soluble. This feature provides advantages over traditional silicon hydrogel monomer mixtures in that there is less risk of incompatibility phase separation resulting in hazy lenses. Also, the polymerized materials are extractable with water. However, when desired traditional organic extraction methods may also be used. In addition, the extracted lenses demonstrate a good combination of oxygen permeability (Dk) and low modulus, properties known to be important to obtaining desirable contact lenses. Suitable water contents for materials made with the monomers of the invention herein would range from 0 wt % to about 80 wt %. Suitable oxygen permeability (Dk) would range from about 10 to about 200. Suitable modulus would range from about 20 g/mm$^2$ to about 2000 g/mm$^2$. Moreover, lenses prepared with the quaternized silicon monomers of the invention herein are wettable even without surface treatment, provide dry mold release, do not require solvents in the monomer mix (although solvents such as glycerol may be used), the extracted polymerized material is not cytotoxic and the surface is lubricious to the touch. In cases where the polymerized monomer mix containing the quaternized silicon monomers of the invention herein do not demonstrate a desirable tear strength, toughening agents such as TBE (4-t-butyl-2-hydroxycyclohexyl methacrylate) may be added to the monomer mix. Other strengthening agents are well known to those of ordinary skill in the art and may also be used when needed.

Although an advantage of the cationic silicon-containing monomers disclosed herein is that they are relatively water soluble and also soluble in their comonomers, an organic diluent may be included in the initial monomeric mixture. As used herein, the term "organic diluent" encompasses organic compounds which minimize incompatibility of the components in the initial monomeric mixture and are substantially nonreactive with the components in the initial mixture. Additionally, the organic diluent serves to minimize phase separation of polymerized products produced by polymerization of the monomeric mixture. Also, the organic diluent will generally be relatively non-inflammable.

Contemplated organic diluents include tert-butanol (TBA); diols, such as ethylene glycol and polyols, such as glycerol. Preferably, the organic diluent is sufficiently soluble in the extraction solvent to facilitate its removal from a cured article during the extraction step. Other suitable organic diluents would be apparent to a person of ordinary skill in the art.

The organic diluent is included in an amount effective to provide the desired effect. Generally, the diluent is included at 5 to 60% by weight of the monomeric mixture, with 10 to 50% by weight being especially preferred.

According to the present process, the monomeric mixture, comprising at least one hydrophilic monomer, at least one cationic silicon-containing monomer and optionally the organic diluent, is shaped and cured by conventional methods such as static casting or spincasting.

Lens formation can be by free radical polymerization such as azobisisobutyronitrile (AIBN) and peroxide catalysts using initiators and under conditions such as those set forth in U.S. Pat. No. 3,808,179, incorporated herein by reference. Photo initiation of polymerization of the monomer mixture as is well known in the art may also be used in the process of forming an article as disclosed herein. Colorants and the like may be added prior to monomer polymerization.

Subsequently, a sufficient amount of unreacted monomer and, when present, organic diluent is removed from the cured article to improve the biocompatibility of the article. Release of non-polymerized monomers into the eye upon installation of a lens can cause irritation and other problems. Unlike other monomer mixtures that must be extracted with flammable solvents such as isopropyl alcohol, because of the properties of the novel quaternized siloxane monomers disclosed herein, non-flammable solvents may be used for the extraction process.

Once the biomaterials formed from the polymerized monomer mix containing the cationic silicon containing monomers disclosed herein are formed they are then extracted to prepare them for packaging and eventual use. Extraction is accomplished by exposing the polymerized materials to various solvents such as water, tert-butanol, etc. for varying periods of time. For example, one extraction process is to immerse the polymerized materials in water for about three minutes, remove the water and then immerse the polymerized materials in another aliquot of water for about three minutes, remove that aliquot of water and then autoclave the polymerized material in water or buffer solution.

Following extraction of unreacted monomers and any organic diluent, the shaped article, for example an RGP lens, is optionally machined by various processes known in the art. The machining step includes lathe cutting a lens surface, lathe cutting a lens edge, buffing a lens edge or polishing a lens edge or surface. The present process is particularly advantageous for processes wherein a lens surface is lathe cut, since machining of a lens surface is especially difficult when the surface is tacky or rubbery.

Generally, such machining processes are performed before the article is released from a mold part. After the machining operation, the lens can be released from the mold part and hydrated. Alternately, the article can be machined after removal from the mold part and then hydrated. Ophthalmic monomers of the type described are prepared using the two step synthetic procedure detailed below, such that R1 is CH3 or O(Si[CH3]3), R2 is the same as R1 or H(Si[CH3]2O)n, X is Cl, Br, or I, R3 is CH3, a straight or branched alkyl chain, linker group L is a straight or branched alkyl chain, ester, amide, ether, ureido, urethane, carbamate, or a combination thereof, R4 is CH3, H, or F, and R5 is H or F.

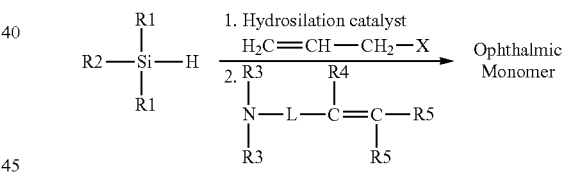

EXAMPLES

Example 1

General Ophthalmic Monomer Preparation

Hydride containing siloxane compound is dissolved in a solvent or combination of solvents and treated with allylic halide and a standard hydrosilation catalyst known in the art, and is heated under a nitrogen atmosphere for a sufficient time to result in the quantitative loss of reactants as determined by GC, NMR, or other appropriate analytical technique. The cooled solution is then concentrated at reduced pressure and optionally purified by one of or a combination of techniques to remove residual catalyst and/or other contaminants, including column chromatography, liquid-liquid extraction, and distillation. The resulting material is dissolved in a solvent appropriate for nucleophilic substitution, treated with the desired tertiary amino-vinyl compound, and heated at a temperature sufficient to promote reaction without causing gelation. Solvents are removed at reduced pressure and the resulting material can be purified by one of or combinations of several techniques well known in the art, including vacuum-stripping, liquid-liquid extraction, and column chromatography.

Example 2

Analytical Measurements

NMR: $^1$H-NMR characterization was carried out using a 400 MHz Varian spectrometer using techniques standard in the art. Samples were dissolved in chloroform-d (99.8 atom % D) at a concentration of 20 mg/mL, unless otherwise noted. Chemical shifts were determined by assigning the residual chloroform peak at 7.25 ppm. Peak areas were determined by integration of baseline separated peaks, and are reported as a ratio of the total normalized area of all product peaks rounded to the nearest 0.01. Splitting patterns (s=singlet, d=doublet, t=triplet, q=quartet, m=multiplet, br=broad) and coupling constants (J/Hz) are reported when present and clearly distinguishable, but as one skilled in the art can appreciate, a lack of reported splitting does not necessarily indicate a lack of splitting in the disclosed ophthalmic monomers.

Mechanical properties and Oxygen Permeability: Modulus and elongation tests were conducted according to ASTM D-1708a, employing an Instron (Model 4502) instrument where the hydrogel film sample is immersed in borate buffered saline; an appropriate size of the film sample is gauge length 22 mm and width 4.75 mm, where the sample further has ends forming a dog bone shape to accommodate gripping of the sample with clamps of the Instron instrument, and a thickness of 200+50 microns.

Oxygen permeability (also referred to as Dk) was determined by the following procedure. Other methods and/or instruments may be used as long as the oxygen permeability values obtained therefrom are equivalent to the described method. The oxygen permeability of silicone hydrogels is measured by the polarographic method (ANSI Z80.20-1998) using an O2 Permeometer Model 201T instrument (Createch, Albany, Calif. USA) having a probe containing a central, circular gold cathode at its end and a silver anode insulated from the cathode. Measurements are taken only on pre-inspected pinhole-free, flat silicone hydrogel film samples of three different center thicknesses ranging from 150 to 600 microns. Center thickness measurements of the film samples may be measured using a Rehder ET-1 electronic thickness gauge. Generally, the film samples have the shape of a circular disk. Measurements are taken with the film sample and probe immersed in a bath containing circulating phosphate buffered saline (PBS) equilibrated at 35° C.+/−0.2°. Prior to immersing the probe and film sample in the PBS bath, the film sample is placed and centered on the cathode premoistened with the equilibrated PBS, ensuring no air bubbles or excess PBS exists between the cathode and the film sample, and the film sample is then secured to the probe with a mounting cap, with the cathode portion of the probe contacting only the film sample. For silicone hydrogel films, it is frequently useful to employ a Teflon polymer membrane, e.g., having a circular disk shape, between the probe cathode and the film sample. In such cases, the Teflon membrane is first placed on the premoistened cathode, and then the film sample is placed on the Teflon membrane, ensuring no air bubbles or excess PBS exists beneath the Teflon membrane or film sample. Once measurements are collected, only data with correlation coefficient value (R2) of 0.97 or higher should be entered into the calculation of Dk value. At least two Dk measurements per thickness, and meeting R2 value, are obtained. Using known regression analyses, oxygen permeability (Dk) is calculated from the film samples having at least three different thicknesses. Any film samples hydrated with solutions other than PBS are first soaked in purified water and allowed to equilibrate for at least 24 hours, and then soaked in PUB and allowed to equilibrate for at least 12 hours. The instruments are regularly cleaned and regularly calibrated using RGP standards. Upper and lower limits are established by calculating a +/−8.8% of the Repository values established by William J. Benjamin, et al., The Oxygen Permeability of Reference Materials, Optom Vis Sci 7 (12s): 95 (1997), the disclosure of which is incorporated herein in its entirety:

| Material Name | Repository Values | Lower Limit | Upper Limit |
| --- | --- | --- | --- |
| Fluoroperm 30 | 26.2 | 24 | 29 |
| Menicon EX | 62.4 | 56 | 66 |
| Quantum II | 92.9 | 85 | 101 |

Unless otherwise specifically stated or made clear by its usage, all numbers used in this application should be considered to be modified by the term "about."

Films were removed from glass plates and hydrated/extracted in deionized $H_2O$ for a minimum of 4 hours, transferred to fresh deionized H2O and autoclaved 30 min at 121° C. The cooled films were then analyzed for selected properties of interest in ophthalmic materials as described in table 2. Mechanical tests were conducted in borate buffered saline according to ASTM D-1708a, discussed above. The oxygen permeabilities, reported in Dk (or barrer) units, were measured in phosphate buffered saline at 35° C., using acceptable films with three different thicknesses, as discussed above.

ABBREVIATIONS

NVP 1-Vinyl-2-pyrrolidone
DMA N,N-Dimethylacrylamide
TRIS Methacryloxypropyltris(trimethylsiloxy)silane
HEMA 2-Hydroxyethyl methacrylate
AIBN 2,2'-Azobis(2-methylpropionitrile)
Darocur 2-Hydroxy-2-methylpropiophenone
TBA Tert-butanol
TBE 4-Tertbutyl-2-hydroxy-cyclohexyl methacrylate
MMA Methyl methacrylate

Example 3

Reagents

The reagents allyl bromide, 2-(dimethylamino)ethyl methacrylate, platinum-1,3-divinyl-1,1,3,3-tetramethyldisiloxane complex in xylenes, N,N-dimethylacrylamide, 2,2'-azobis(2-methylpropionitrile), chloroform-d, tert-butanol, methyl methacrylate, and all solvents were purchased from Sigma-Aldrich, Milwaukee, Wis., and used without further purification. 1-Vinyl-2-pyrrolidone and 2-hydroxyethyl methacrylate were purchased from Sigma-Aldrich, Milwaukee, Wis., and distilled prior to use. 4-tertbutyl-2-hydroxycyclohexyl methacrylate was obtained from Aron Chemicals. The reagents tris(trimethylsiloxy)silane, methacryloxypropyltris(trimethylsiloxy)silane and hydride terminated poly(dimethylsiloxane) (average molecular weight 1000-1100 g/mol) were purchased from Gelest, Inc., Morrisville, Pa.

Preparation of Ophthalmic Monomer 1.

Allyl bromide (40 mL, 0.46 mol) and tris(trimethylsiloxy) silane (168 mL, 0.48 mol) in 2:1 (v/v) tetrahydrofuran/dioxane solution (920 mL) was treated with 10% platinum-1,3-divinyl-1,1,3,3-tetramethyldisiloxane complex in xylenes (1.2 mL) and heated at 60° C. for 15 hours under nitrogen atmosphere. The cooled solution was concentrated under reduced pressure, divided into two parts, passed through a silica gel column (5×20 cm, pentane), recombined, and solvents again removed under reduced pressure. The resulting colorless liquid was dissolved in ethyl acetate (375 mL), treated with 2-(dimethylamino)ethyl methacrylate (71 mL, 0.42 mol), and heated at 60° C. in the dark. Conversion was monitored using GC. After approximately 50 hours, the solution was cooled to ambient temperature at which time a crystalline solid precipitated from solution. The precipitate was filtered and recrystallized from ethyl acetate twice to afford ophthalmic monomer 1 as a colorless, crystalline solid (109.2 g): $^1$H NMR (CDCl$_3$, 400 MHz) δ 6.13 (s, 0.02H), 5.66 (s, 0.02H), 4.65-4.63 (m, 0.04H), 4.18-4.16 (m, 0.04H), 3.69-3.62 (m, 0.08H), 3.49 (s, 0.12H), 1.93-1.82 (m, 0.12H), 1.62-1.56 (m, 0.04H), 0.09 (s, 0.51H); mp 114-116° C. The proton NMR spectrum of ophthalmic monomer 1 is included as FIG. 1.

TABLE 1

Photopolymerization of transparent articles containing ophthalmic monomer 1

| ID | Monomers 1 | NVP | DMA | TRIS | EGDMA | Glycerol | Darocur |
|---|---|---|---|---|---|---|---|
| A | 24.8 | | 74.5 | | 0.4 | | 0.3 |
| B | 42.2 | | 42.2 | | 0.4 | 15.1 | 0.2 |
| C | 57.9 | 31.2 | | | 0.5 | 10.1 | 0.3 |
| D | 53.6 | 35.7 | | | 0.4 | 10.0 | 0.3 |
| E | 33.0 | 33.2 | | 33.2 | 0.4 | | 0.4 |

Example 5

Thermal Polymerization of Articles Containing Ophthalmic Monomer 1

Liquid monomer solutions containing ophthalmic monomer 1 were clamped between silanized glass plates at various thicknesses and polymerized using thermal decomposition of the free-radical generating additive by heating 2 h at 100° C. under a nitrogen atmosphere. Each of the representative formulation examples listed in table 2 afforded a transparent, tack-free, insoluble film.

TABLE 2

Thermal polymerization of transparent articles containing ophthalmic monomer 1.

| ID | 1 | TRIS | NVP | HEMA | TBE | EGDMA | MMA | Glycerol | TBA | v-64 |
|---|---|---|---|---|---|---|---|---|---|---|
| F | 47.6 | | 31.9 | | | 0.3 | | 19.8 | | 0.4 |
| G | 55.5 | | 23.9 | | | 0.3 | | 19.9 | | 0.4 |
| H | 47.1 | | 31.5 | | | 0.3 | | 20.6 | | 0.4 |
| I | 47.8 | | 31.8 | | 5.0 | | | 15.0 | | 0.4 |
| J | 57.1 | | 24.6 | | | 1.1 | | 16.7 | | 0.5 |
| K | 33.0 | 33.0 | 33.4 | | | 0.3 | | | | 0.3 |
| L | 28.1 | 28.1 | 28.2 | | | 0.3 | | | 14.9 | 0.4 |
| M | 28.1 | 14.3 | 28.0 | | | 0.4 | 13.6 | 15.1 | | 0.5 |
| N | 21.9 | | 22.4 | 43.9 | | 0.3 | | 10.9 | | 0.5 |
| O | 16.7 | 17.1 | 17.1 | 33.0 | | 0.7 | | | 14.8 | |
| P | 17.8 | 17.9 | 17.9 | 35.7 | | 0.3 | | | 9.9 | 0.5 |

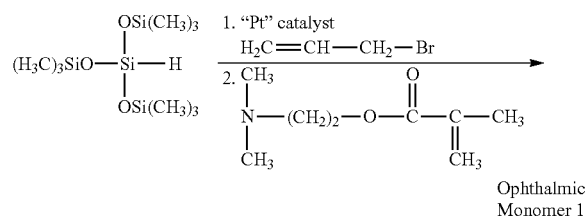

Ophthalmic Monomer 1

Example 4

Photopolymerization of Articles Containing Ophthalmic Monomer 1

Liquid monomer solutions containing ophthalmic monomer 1 were clamped between silanized glass plates at various thicknesses and polymerized using photochemical decomposition of the free-radical generating additive. Each of the examples listed in table 1 represents a formulation that resulted in a transparent, tack-free, insoluble film.

Example 6

Properties of Processed Articles Containing Ophthalmic Monomer 1

Representative films containing ophthalmic monomer 1 from examples above were subjected to hydration and extraction in deionized water for a minimum of 4 h, then followed by autoclave sterilization also in deionized water. Properties of interest for ophthalmic applications were then determined (Table 3).

TABLE 3

Selected Properties of processed articles containing ophthalmic monomer 1.

| ID | Water content (%) | Dk (barrers) | Modulus (g/mm$^2$) | Tear (g/mm) |
|---|---|---|---|---|
| O | 62 | | 151 | |
| P | 71 | | 56 | 1.4 |
| L | 66 | 90 | 100 | 11 |

Example 7

Preparation of Ophthalmic Monomer 2

To a solution of hydride terminated poly(dimethylsiloxane) (99.3 g, 1000-1100 $M_n$) and allyl bromide (25 mL, 287 mmol) in tetrahydrofuran/1,4-dioxane (2:1 v/v, 570 mL) under nitrogen atmosphere was added 10% platinum-1,3-divinyl-1,1,3,3-tetramethyldisiloxane complex in xylenes (0.7 mL) and the solution was heated 15 h at 60° C. The cooled solution was concentrated under reduced pressure, redissolved in pentane (250 mL), stirred 15 h over silica gel (40 g), filtered and solvents removed again under reduced pressure. The colorless liquid was then dissolved in ethyl acetate (140 mL), treated with 2-(dimethylamino)ethyl methacrylate (94 mL, 557 mmol) and heated 100 h at 60° C. under nitrogen atmosphere and in the dark. The cooled solution was vacuum stripped to remove solvent and residual 2-(dimethylamino)ethyl methacrylate, affording ophthalmic monomer 2 as a waxy solid (99.4 g): $^1$H NMR (CDCl$_3$, 400 MHz) δ 6.19 (s, 0.01H), 5.66 (s, 0.01), 4.64 (br, 0.02H), 1.76 (br, 0.02H), 3.70-3.64 (m, 0.04H), 3.50 (0.06H), 1.94-1.83 (m, 0.05H), 1.63-1.55 (m, 0.02H), 0.05 (s, 0.78H). The proton NMR spectrum of ophthalmic monomer 2 is substantially similar in appearance to that of ophthalmic monomer 1 as demonstrated in FIG. 1 except with respect to peak area integration ratios.

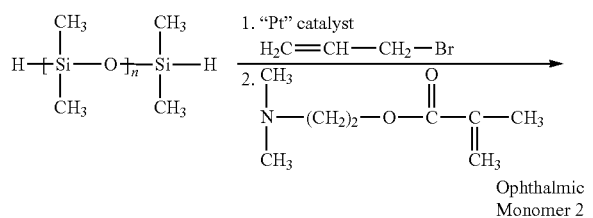

Ophthalmic Monomer 2

Example 8

Thermal Polymerization of Articles Containing Ophthalmic Monomer 2

Liquid monomer solutions containing ophthalmic monomer 2 were clamped between silanized glass plates at various thicknesses and polymerized using thermal decomposition of the free-radical generating additive by heating 2 h at 100° C. under a nitrogen atmosphere. Each of the representative formulation examples listed in table 4 afforded a transparent, tack-free, insoluble film.

TABLE 4

Thermal polymerization of transparent articles containing ophthalmic monomer 2.

| ID | Monomer 2 | NVP | DMA | HEMA | TRIS | TBE | v-64 | Glycerol |
|---|---|---|---|---|---|---|---|---|
| Q | 49.8 | | | 49.7 | | | 0.5 | |
| R | 24.9 | | 49.8 | | 24.9 | | 0.5 | |
| S | 24.9 | | 49.7 | 10 | 24.9 | | 0.5 | |
| T | 24.9 | | 49.7 | | 24.9 | | 0.5 | |
| U | 39.8 | | 39.8 | | 19.9 | | 0.5 | |
| V | 35.3 | | 35.3 | | 17.6 | | 0.5 | 11.3 |
| W | 29.7 | 39.5 | | 10.1 | 20.2 | | 0.5 | |
| X | 24.9 | 39.8 | | 10.0 | 24.9 | | 0.5 | |
| Y | 23.6 | 37.8 | | 9.5 | 23.6 | 5.0 | 0.5 | |
| Z | 22.4 | 35.8 | | 9.0 | 22.4 | 10.0 | 0.5 | |
| AA | 14.9 | 49.8 | | 10.1 | 24.8 | | 0.4 | |
| AB | 14.9 | 39.8 | | 20.0 | 24.9 | | 0.5 | |

Example 9

Properties of Processed Articles Containing Ophthalmic Monomer 2

Representative films containing ophthalmic monomer 2 from examples above were subjected to hydration and extraction in deionized water for a minimum of 4 h, then followed by autoclave sterilization also in deionized water. Properties of interest for ophthalmic applications were then determined (Table 5).

TABLE 5

Selected Properties of processed articles containing ophthalmic monomer 2.

| ID | Water (%) | Dk (barrers) | Modulus (g/mm$^2$) | Tear (g/mm) |
|---|---|---|---|---|
| Q | 30 | 37 | 231 | |
| R | 50 | 51 | 60 | 2 |
| S | 51 | 70 | 79 | 2 |
| V | 56 | 64 | 75 | 2 |
| Y | 59 | ND | 100 | 3 |
| Z | 54 | | 248 | 9 |
| AA | | 68 | 34 | 1 |
| AB | 64 | 54 | 45 | 2 |

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. A biomedical device obtained from a polymerization product of a monomer mixture comprising a water extractable biomedical device forming cationic non-hydroxyl-containing organosilicon-containing monomer, wherein the water extractable medical device forming cationic non-hydroxyl-containing organosilicon-containing monomer is obtained by the method comprising
   (a) dissolving a hydride containing siloxane compound in a solvent or combination of solvents;
   (b) treating the dissolved hydride containing siloxane compound with an allylic halide and a hydrosilation catalyst to form a first reaction mixture;
   (c) heating the first reaction mixture under a nitrogen atmosphere for a sufficient time to result in the quantitative loss of reactants as determined by appropriate analytical technique thus providing a monomer mixture;
   (d) cooling the monomer mixture;
   (e) concentrating the cooled mixture;
   (f) dissolving the cooled mixture in a solvent appropriate for nucleophilic substitution;

(g) treating the cooled mixture containing the solvent appropriate for nucleophilic substitution with a tertiary amino-vinyl compound to form a second reaction mixture;

(h) heating the second reaction mixture at a temperature sufficient to promote reaction without causing gelation;

(i) removing any remaining solvent to provide a product containing material; and, (j) purifying the product containing material to yield the water extractable medical device forming cationic non-hydroxyl-containing organosilicon-containing monomer.

2. The biomedical device of claim 1, wherein the hydride containing siloxane compound is tris(trimethylsiloxy) silane or a hydride terminated poly(dimethylsiloxane), the allylic halide is allyl bromide and the tertiary amino-vinyl compound is 2-(dimethylamino)ethyl methacrylate.

3. The biomedical device of claim 1, wherein the monomer mixture further comprises a second comonomer.

4. The biomedical device of claim 1, wherein the second monomer is selected from the group consisting of an unsaturated carboxylic acid, acrylic substituted alcohol, vinyl lactam, acrylamide, methacrylate, hydrophilic vinyl carbonate, hydrophilic vinyl carbamate monomer, hydrophilic oxazolone monomer and mixtures thereof.

5. The biomedical device of claim 3, wherein the second monomer is selected from the group consisting of methacrylic acid, acrylic acid, 2-hydroxyethylmethacrylate, 2-hydroxyethylacrylate, N-vinyl pyrrolidone, N-vinyl caprolactone, methacrylamide, N,N-dimethylacrylamide, ethylene glycol dimethacrylate, methyl methacrylate, allyl methacrylate, 3-methacryloylpropyl tris(trimethylsiloxyl) silane and mixtures thereof.

6. The biomedical device of claim 1, wherein the device is a contact lens.

7. The biomedical device of claim 6, wherein the contact lens is a rigid gas permeable contact lens, a soft contact lens or a hydrogel contact lens.

8. The biomedical device of claim 1, wherein the device is an intraocular lens.

9. The biomedical device of claim 1, wherein the device is a corneal implant.

10. A biomedical device obtained from a polymerization product comprising a monomer mixture comprising a cationic non-hydroxyl-containing organosilicon-containing monomer, wherein the cationic organosilicon-containing monomer is obtained by a method comprising:

(a) treating a solution comprising a hydride containing siloxane compound in a first solvent with an allylic halide in the presence of a hydrosilation catalyst; and (b) treating the product of step (a) with a tertiary amino-vinyl compound.

11. The biomedical device of claim 10, wherein the hydride containing siloxane compound is tris(trimethylsiloxy) silane or a hydride terminated poly(dimethylsiloxane), the allylic halide is allyl bromide and the tertiary amino-vinyl compound is 2-(dimethylamino)ethyl methacrylate.

12. The biomedical device of claim 10, wherein the monomer mixture further comprises a second comonomer.

13. The biomedical device of claim 10, wherein the second comonomer is selected from the group consisting of an unsaturated carboxylic acid, acrylic substituted alcohol, vinyl lactam, acrylamide, methacrylate, hydrophilic vinyl carbonate, hydrophilic vinyl carbamate monomer, hydrophilic oxazolone monomer and mixtures thereof.

14. The biomedical device of claim 12, wherein the monomer mixture further comprising in addition to the second monomer a hydrophobic monomer and a hydrophilic monomer.

15. The biomedical device of claim 10, wherein the device is a contact lens.

16. The biomedical device of claim 10, wherein the device is selected from the group consisting of heart valves, intraocular lenses, films, surgical devices, vessel substitutes, intrauterine devices, membranes, diaphragms, surgical implants, blood vessels, artificial ureters, artificial breast tissue, membranes for kidney dialysis machines, membranes for heart/lung machines, catheters, mouth guards, denture liners, ophthalmic devices, and contact lenses.

* * * * *